United States Patent
Sohn et al.

(10) Patent No.: US 6,221,906 B1
(45) Date of Patent: Apr. 24, 2001

(54) PLATINUM COMPLEX CONJUGATED TO CYCLOTRIPHOSPHAZENE, ITS PREPARATION, AND ANTICANCER AGENT COMPRISING THE SAME

(75) Inventors: Youn Soo Sohn; Hyoung Gee Baek; Chong Ock Lee, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/517,718

(22) Filed: Mar. 2, 2000

(30) Foreign Application Priority Data

Mar. 26, 1999 (KR) .................................................. 99-10532

(51) Int. Cl.[7] .............................. A61K 31/28; C07F 15/00
(52) U.S. Cl. .............................. 514/492; 556/20; 556/137
(58) Field of Search ....................... 556/20, 137; 514/492

(56) References Cited

U.S. PATENT DOCUMENTS

| | | | |
|---|---|---|---|
| 5,616,613 | * | 4/1997 | Kawai et al. .......................... 514/492 |
| 5,744,497 | * | 4/1998 | Valsecchi et al. .................... 514/492 |
| 5,747,534 | * | 5/1998 | Gunther et al. ....................... 514/492 |
| 5,922,689 | * | 7/1999 | Shaw ....................................... 514/45 |
| 6,001,872 | * | 12/1999 | Farrell et al. .......................... 514/492 |
| 6,022,892 | * | 2/2000 | Farrell et al. .......................... 514/492 |

OTHER PUBLICATIONS

Cleare et al., 1978 "Anti–Tumour Platinum Complexes: Relationships Between Chemical Properties and Activity" Biochimie 60: 835–850.

Douple, 1984 "CIS–Diamminedichloroplatinum (II): Effects of a Representative Metal Coordination Complex on Mammalian Cells", Pharmac. Ther. 25: 297–326.

Harrison et al., 1980 "An Efficient Route for the Preparation of Highly Soluble Platinum (II) Antitumour Agents" Inorganica Chemica Acta. 46: L15–L16.

Rosenberg et al., 1965 "Inhibition of Cell Division in Escherichja Coli by Electrolysis Products from a Platinum Electrode" Nature 205: 698–699.

Sherman et al., 1987 "Structural Aspects of Platinum Anticancer Drug Interactions with DNA" Chem. Rev. 87: 1153–1181.

* cited by examiner

*Primary Examiner*—Porfirio Nazario-Gonzalez
(74) *Attorney, Agent, or Firm*—Morrison & Foerster LLP

(57) ABSTRACT

The present invention relates to a platinum complex conjugated to a cyclotriphosphazene represented by Formula 1 and a preparation method thereof. The platinum complex according to the present invention can be used as an anticancer agent.

8 Claims, No Drawings

PLATINUM COMPLEX CONJUGATED TO CYCLOTRIPHOSPHAZENE, ITS PREPARATION, AND ANTICANCER AGENT COMPRISING THE SAME

BACKGROUND OF THE INVENTION

The present invention relates to an anticancer platinum complex conjugated to cyclotriphosphazene represented by Formula 1, which has a prominent anticancer activity when administered via injection, and a preparation method thereof.

Formula 1

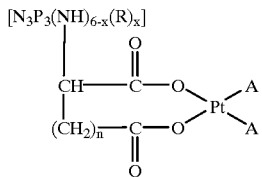

(wherein $N_3P_3$ is a cyclotriphosphazene backbone

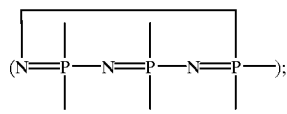

R is a solubilizing agent selected from the group consisting of methylamine, methoxy and amino acid;

A is monodentate neutral ligand, ammonia ($NH_3$) or as

represents a bidentate chelating diamine selected from the group consisting of ethylenediamine ($NH_2CH_2CH_2NH_2$)(en), 2,2-dimethyl-1,3-propanediamine ($NH_2CH_2CH(CH_3)_2CH_2NH_2$)(dmpda), 2,2-bisaminomethylpropanediol ($NH_2CH_2C(CH_2OH)_2CH_2NH_2$)(bampd), and trans-(±)-1,2-diaminocyclohexane

n is the number defining the kind of anionic amino carboxylic acids and is an integer from 0 to 2; wherein 0 for amino malonic acid derivatives, 1 for aspartic acid derivatives and 2 for glutamic acid derivatives; and x is a value between 0 and 3).

The present inventors have found that the platinum complex conjugated to cyclotriphosphazene as represented by the above Formula 1 is a novel compound that has superior anticancer activities especially having a controlled-releasing property when administered via injection.

Since the anticancer activity of cisplatin, cis-$(NH_3)_2PtCl_2$, was reported by B. Rosenberg of USA (Nature 205, 698 (1965)), it has been officially proven as one of the most efficient anticancer drugs for many types of carcinomas including testicular, ovarian, bladder, and head and neck cancers. However, its use is limited due to its high toxicity ($LD_{50}$=13 mg/kg, M. J. Cleare, Biochimie 60, 835(1978)). On the other hand, a second generation anticancer agent, carboplatin(cis-$(NH_3)_2Pt(CBDCA)$ (CBDCA=1,1-cyclobutane dicarboxylate), which was approved by the FDA in 1989, has much lower toxicity($LD_{50}$=180 mg/kg, M. J. Cleare, Biochimie 60, 835(1978)) than cisplatin, but is not widely used because carboplatin is more expensive and has lower anticancer activity than cisplatin. Therefore, researches, too numerous to mention, are being performed worldwide without much success to find a third generation anticancer drug that has a higher anticancer activity and a lower toxicity than cisplatin. Also the third generation anticancer drug should not have any cross-resistance to cisplatin or carboplatin, and must be water-soluble as well as chemically stable. Because of such many requirements, the third generation anticancer drug has not been commercialized yet, although there are more than 10 candidate compounds that are currently under clinical trials.

The mechanism of anticancer activity and toxicity of cisplatin has not been fully understood up to date. To summarize the research findings, even though some of the cisplatin molecules are partially hydrolyzed, most of them remain as neutral molecules due to the high chloride concentration(>100 mM) in the plasma, and therefore easily diffuse through cell membrane. Inside the cell, the chlorine ion is dissociated from the cisplatin molecule by hydrolysis since the chloride concentration is low (4 mM) in the cytoplasm. The cells are killed because DNA replication is prohibited as a result of complex formation between (diamine)platinum cation and DNA. The cytotoxicity of the platinum complex is exhibited since the drug molecules cannot distinguish between cancer cells and normal cells. The relationship, however, between the molecular structure of the platinum complex and the in vivo anticancer activity is not fully understood. The present inventors have developed a polymeric platinum complex by conjugating the active platinum (II) moiety to a biodegradable polyphosphazene bearing a solubilizing agent, which exhibited outstanding anticancer activity with lower toxicity. However, the polymeric platinum complex has been found to response positively to the anaphylaxis test, and therefore, could not be commercialized.

SUMMARY OF THE INVENTION

To develop a new third generation anticancer drug with higher anticancer activity and lower toxicity than cisplatin and without anaphylactic reaction, the present inventors have synthesized an oligomeric platinum complex by substitution reaction of hexachlorocyclotriphosphazene with a solubilizing agent and a dicarboxylic amino acid derivative as a spacer for the platinum complex. The newly formed oligomeric platinum complex has a lower toxicity(mouse $LD_{50}$=125~250 mg/kg) compared to cisplatin ($LD_{50}$=13 mg/kg) and higher anticancer activity (ILS(%)≧500). Moreover, this novel compound has a great advantage of wider spectrum of activity because it shows a high anticancer activity to non-small cell lung cancer that is not cured by cisplatin based regimens. Furthermore, this oligomeric new compound also dose not exhibit anaphylactic reaction unlike the polymeric platinum complex anticancer agent developed previously by the present inventors. When drugs are administered by injection, some bioincompatible drugs may rapidly bind to proteins resulting in anaphylaxis. Most polyphosphazene-platinum conjugates have been found to show positive anaphylactic reaction. On the other hand, platinum complex conjugated to oligomeric cyclotriphosphazene has been found to show good biocompatibility without anaphylactic reaction and the polymer backbone was found to degrade slowly in the body with controlled release of the antitumor platinum moiety so as to maintain the optimal effective concentration for outstanding antitumor activity.

DETAILED DESCRIPTION OF THE INVENTION

The preparation method of the new platinum complex conjugated to cyclotriphosphazene of Formula 1 comprises of the following steps. (1) A dicarboxylic amino acid ester is conjugated as a spacer to hexachloro-cyclotriphosphazene ($N_3P_3Cl_6$). (2) When necessary, a compound of Formula 2, to which a hydrophilic or lipophilic organic group R is conjugated as a solubilizing agent is obtained. (3) The conjugated amino acid ester is hydrolyzed in the presence of alkali to obtain alkali metal salt of formula 3.

Formula 2

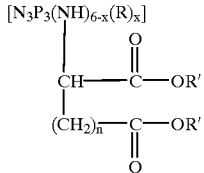

Formula 3

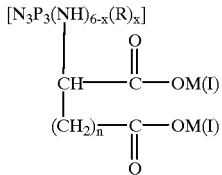

Formula 4

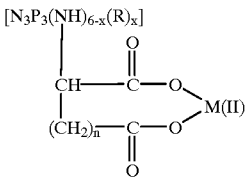

Formula 5

Formula 6

(R, A, n and x in Formulas 2, 3, 4, 5 and 6 are identical to those defined in Formula 1;

R' is a methyl or ethyl group;

M(I) is an alkali metal ion such as sodium ion or lithium ion;

M(II) is an alkaline earth metal ion such as barium ion or calcium ion;

$L_2$ is selected from two $NO_3^-$ ions or a single $SO_4^{2-}$ ion), (4) The cyclotriphosphazene derivatives containing hydrolyzed amino acid of Formula 3 has a high water solubility and can be directly reacted with platinum intermediate of Formula 5 in aqueous solution, but the alkali metal salt of Formula 3 may be reacted with an alkaline earth metal salt to obtain alkaline earth metal salt of Formula 4, which is then reacted with a water-soluble (diamine) platinum salt of Formula 5, to obtain a platinum complex conjugated to cyclotriphosphazene of Formula 1.

The water-soluble (diamine)platinum(II) salts of Formula 5 can be obtained by reacting (diamine)platinum iodide of Formula 6 with the corresponding salt of silver according to the procedures in the literature(R. C. Harrison. lnorg. Chimica Acta 46, L15(1980)).

The (diamine)platinum(II) iodide of Formula 6 can be easily obtained by reacting potassium tetrachloroplatinate, potassium iodide and the corresponding diamine according to the literature(M. J. Cleare, Biochimie 60, 835(1978)).

The preparation procedure of the oligomeric platinum complex anticancer agent of Formula 1 is composed of two steps: (1) substitution of hexachlorocyclotriphosphazene with a solubilizing agent and a spacer group for platination and (2) conjugation of the platinum complex to the spacer group, dicarboxylic amino acid. For illustration in more details, hexachloro-cyclotriphosphazene($N_3P_3Cl_6$) is dissolved in anhydrous benzene or toluene with excess triethylamine as a hydrogen chloride acceptor. To this solution, methyl or ethyl ester of amino malonic acid, aspartic acid, or glutamic acid as a spacer for platinum complex is slowly added in 3~9 moles per mole of the above trimer, and stirred for 3~10 hours at room temperature and then refluxed for more than 24 hours. After filtering out the triethylamine hydrochloride salt, a solubilizing agent (methanol, methylamine or amino acid ester) and equimolar triethylamine are added to the filtrate, which is stirred for additional 4~10 hours at 60~70° C. After evaporation of the solvent at reduced pressure, the reactant is purified by silica gel (mesh, 230~400) column chromatography using dichloromethane as an eluant to remove unreacted amino acid ester and side products to obtain the compound of Formula 2. To this compound, an aqueous solution containing 2~3 equivalent weight of a hydroxide of alkali metals such as sodium or lithium or alkaline earth metals such as calcium or barium per mole of the substituted amino acid is added for hydrolysis for one day at room temperature, and then the product is freeze-dried. To this hydrolysis product, an excess amount of methanol is added and stirred to obtain the amino acid metal salt of Formula 3 or 4 as a precipitate. The precipitate is filtered out and washed with alcohol and ether, and then dried.

The amino acid metal salt of Formula 3 or 4 is reacted with the (diamine)platinum(II) complex intermediate salt which is prepared by the following procedure:Excess potassium iodide is added to an aqueous solution of potassium tetrachloroplatinate and the 1~2 equivalent weight of a desired amine(A) or diamine

is reacted to obtain (diamine)platinum(II) iodide of Formula 6 as a precipitate, Which is filtered and dried. This intermediate product is reacted with equivalent silver salt such as $AgNO_3$ or $Ag_2SO_4$ in aqueous solution for 5~10 hours at room temperature to obtain water soluble (diamine)platinum (II) salt of Formula 5 and silver iodide as a precipitate. This (diamine)platinum(II) salt is reacted with amino acid alkali salt of cyclotriphosphazene of Formula 3 or amino acid alkaline earth metal salt of cyclotiphosphazene of Formula 4 in the mole ratio of 3~6:1 in aqueous solution to obtain (diamine)platinum(II) complex conjugated to the cyclotriphosphazene of Formula 1 by metathesis reaction. As a side-product, alkali metal or alkaline earth metal nitrate or sulfate coexists. To eliminate these side-products, alcohol or acetone can be used as a solvent pair, or the product may be purified using the different solubilities of cyclotriphosphazene platinum complex and the alkali or alkaline earth metal nitrate or sulfate in the reaction solution. For instance, amino acid alkaline earth metal salt of cyclotriphosphazene may be reacted with (diamine)platinum sulfate resulting in insoluble alkaline earth metal sulfate with the water-soluble (diamine)platinum conjugated to the trimer in the pregnant solution. In the case amino acid alkali salt of cyclotriphosphazene is reacted with (diamine)platinum nitrate, the resultant water soluble sodium nitrate coexists with the platinum complex in the reaction solution. However, they can be easily separated by addition of excess alcohol to the reaction solution since sodium nitrate is not soluble in alcohol whereas the platinum complex is soluble also in alcohol. When (diamine)platinum sulfate of Formula 5 and sodium or lithium salt of the cyclotriphosphazene amino acid of Formula 3 are reacted, both water-soluble platinum complex of Formula 1 and sodium sulfate or lithium sulfate are resultant and coexist in the aqueous reaction solution. However, when barium chloride is added to this solution, insoluble barium sulfate precipitates out quantitatively leaving sodium chloride or lithium chloride in the aqueous solution along with the platinum complex of Formula 1. After filtering out barium sulfate, the filtrate may simply be condensed with or without an additional procedure of precipitating out excess sodium chloride or lithium chloride by addition of acetone to obtain the pure platinum complex of Formula 1 as a powder. The platinum complexes of Formula 1 are mostly water-soluble, and therefore improve the formulation problems of cisplatin. Moreover, the anticancer activity of this new compound is superior to carboplatin or cisplatin with lower toxicity. This new compound has a high potential for commercialization as a third generation anticancer drug. The invention will be further illustrated by the following examples, but is not limited to the examples given.

The preparation procedure can be illustrated in the following reaction scheme 1 as below.

Reaction scheme 1

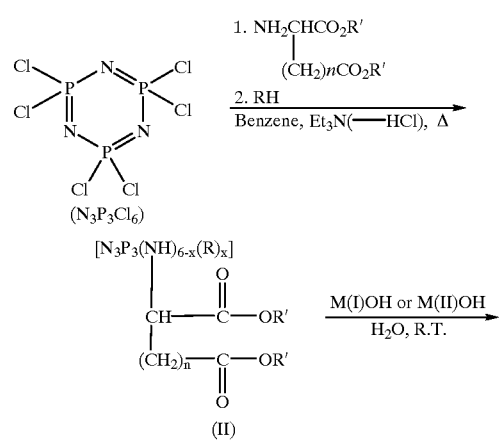

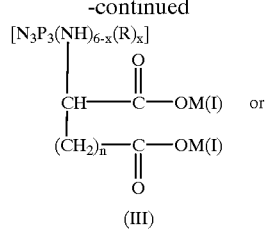

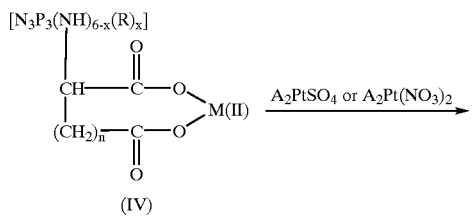

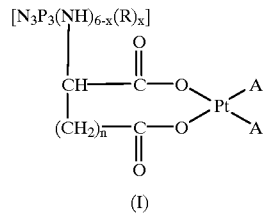

R = NHCH₃, OCH₃,
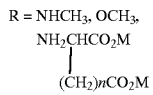
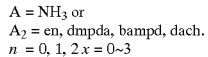
A = NH₃ or
A₂ = en, dmpda, bampd, dach.
n = 0, 1, 2 x = 0~3

EXAMPLE 1.

SYNTHESIS OF [NP(L-Asp·Pt(dach))₂]₃

L-Aspartic acid dimethyl ester hydrochloride (15.4 g, 77.7 mmol) and 10.8 ml(77.7 mmol) of triethylamine were dissolved in 400 ml of toluene and stirred for 5 hours at 50~60° C. After filtering out the resultant precipitate (Et₃N·HCl), 10.8 ml (77.7 mmol) of triethylamine and: 100 ml of toluene solution containing 3.0 g (8.63 mmol) of hexachlorocyclotriphosphazene were slowly added for 30 minutes to the filtrate, which was stirred for 4 hours at room temperature and for an additional 20 hours at 70~80° C. After filtering out the precipitate(Et₃N·HCl), the remaining solvent was evaporated to obtain a viscous product, which was eluted in dichloromethane through a silica gel(mesh, 230~400) column to obtain a purified viscous liquid product [NP(L-Asp~ME₂)₂]₃. Yield:8.0 g (85%).

This aspartate derivative of cyclotriphosphazene(3.0 g, 2.74 mmol) was suspended in 50 ml of aqueous solution containing 49.3 mmol of LiOH and stirred for 24 hours. After the solution was filtered, the filtrate was freeze-dried. The solid product[NP(L-AspLi₂)₂]₃ was washed with sufficient amounts of methanol and ethylether and then dried (yield: 90%).

In the meantime, the platinum intermediate (dach)PtI₂ (3.38 g, 6.0 mmol) and Ag₂SO₄(1.99 g, 6.0 mmol) were reacted in 30 ml of water for 10 hours at room temperature and the resultant precipitate(AgI) was filtered out to obtain the aqueous solution of (dach)PtSO₄. To this solution, 30 ml of cold aqueous solution (0° C.) containing 1.0 mmol of [NP(L-AspLi₂)₂]₃ was added dropwise and stirred in the dark for 20 minutes and stirred for additional 20 minutes at 20° C. To remove Li₂SO₄ from the reaction mixture, 1.46 g(6.0 mmol) of $BaCl_2 \cdot H_2O$ was added to the reaction mixture, which was stirred for 10 minutes. After filtering out $BaSO_4$, 60 ml of acetone was added to the filtrate and stored for 4 hours in the refrigerator. After filtering out the precipitate, 400 ml of acetone was further added to precipitate the final product. The precipitate was filtered, washed with ethylether, and then dried under reduced pressure to obtain a final oligomeric platinum complex.

Molecular formula: $(C_{60}H_{108}N_{21}O_{24}P_3) Pt_6 \cdot 6(H_2O)$

Elemental analysis (%): C, 24.3; H, 4.27; N, 9.58; P, 2.88; Pt, 39.3

Theoretical value: C, 25.0; H, 4.20; N, 10.2; P, 3.23; Pt, 40.7

Proton nuclear magnetic resonance spectrum ($D_2O$, ppm): 1.2~1.4 (4H), 1.6 (2H), 2.2 (2H), 2.5 (2H), 2.8 (2H), 3.7 (1H)

Infrared spectrum (KBr cell, $cm^{-1}$): 516 (m), 816 (m), 1034 (m), 1065 (m), 1172 (m), 1395 (s), 1448 (m), 1578 (s), 3213 (s), 3428 (s)

EXAMPLE 2.

Synthesis of $[NP(L-Asp \cdot Pt(dmpda))_2]_3$

An oligomeric platinum complex was obtained by reacting 3.31 g (6.0 mmol) of $(dmpda)PtI_2$, 1.99 g (6.0 mmol) of $Ag_2SO_4$ and 1.0 g (1.0 mmol) of $[NP(L-Asp \cdot Li_2)_2]_3$ using the same procedure as described in Example 1.

Molecular formula: $(C_{54}H_{108}N_{21}O_{24}P_3)PT_6 \cdot 6(H_2O)$

Elemental analysis (%): C, 22.4; H, 5.01; N, 9.52; P, 2.73; Pt, 40.8

Theoretical value: C, 23.1; H, 4.31; N, 10.5; P, 3.31; Pt, 41.7

Proton nuclear magnetic resonance spectrum ($D_2O$ ppm): 1.1 (6H), 2.2~2.5 (6H), 3.7 (1H)

Infrared spectrum (KBr cell, $cm^{-1}$): 532 (m), 1012 (m), 1044 (m), 1119 (m), 1173 (m), 1221 (m), 1307 (m), 1390 (s), 1479 (m), 1588 (s), 2945 (m), 3224 (m) 3442 (s)

EXAMPLE 3.

Synthesis of $[NP(L-Asp \cdot Pt(bampd))_2]_3$

An oligomeric platinum complex was obtained by reacting 3.50 g (6.0 mmol) of $(bampd)PtI_2$, 1.99 g (6.0 mmol) of $Ag_2SO_4$ and 1.0 g (1.0 mmol) of $[NP(L-Asp \cdot Li_2)_2]_3$ using the same procedure as described in Example 1.

Molecular formula: $(C_{54}H_{108}N_{21}O_{36}P_3)Pt_6 \cdot 6(H_2O)$

Elemental analysis (%): C, 22.8; H, 4.62; N, 10.1; P, 2.62; Pt, 38.2

Theoretical value: C, 21.6; H, 4.03; N, 9.81; P, 3.10; Pt, 39.0

Proton nuclear magnetic resonance spectrum ($D_2O$ ppm): 2.0~2.6 (8H), 3.2 (4H), 3.6 (1H)

Infrared spectrum (KBr cell, $cm^{-1}$): 532 (m), 832 (m), 1044 (m), 1114 (m), 1228 (m), 1339 (s), 1440 (m), 1578 (s), 2925 (m), 3230 (s), 33744 (s)

EXAMPLE 4.

Synthesis of $[NP(L-Asp \cdot Pt(en))_2]_3$

An oligomeric platinum complex was obtained by reacting 3.05 g (6.0 mmol) of $(en)PtI_2$, 1.99 g (6.0 mmol) of $Ag_2SO_4$ and 1.0 g (1.0 mmol) of $[NP(L-Asp \cdot Li_2)_2]_3$ using the same procedure as described in Example 1.

Molecular formula: $(C_{36}H_{72}N_{21}O_{24}P_3)Pt_6 \cdot 6(H_2O)$

Elemental analysis (%): C, 16.1; H, 4.01; N, 10.9; P, 2.95; Pt, 43.4

Theoretical value: C, 16.9; H. 3.31; N, 11.5; P, 3.64; Pt, 45.8

Proton nuclear magnetic resonance spectrum ($D_2O$, ppm): 2.3-2.5 (6H), 3.8 (1H) Infrared spectrum (KBr cell, $cm^{-1}$): 570 (m), 768 (m), 1054 (m), 1135 (m), 1200 (m), 1216 (m), 1291 (m), 1386 (s), 1628 (s), 3258 (s), 3422 (s)

EXAMPLE 5.

Synthesis of $NP(L-Asp \cdot Pt)NH_3)_2)_2]_3$

An oligomeric platinum complex was obtained by reacting 2.90 g (6.0 mmol) of $(NH_3)_2PtI_2$, 1.99 g (6.0 mmol) of $Ag_2SO_4$ and 1.0 g (1.0 mmol) of $[NP(L-Asp \cdot Li_2)_2]_3$ using the same procedure as described in Example 1.

Molecular formula: $(C_{24}H_{60}N_{21}O_{24}P_3)Pt_6 \cdot 6(H_2O)$

Elemental analysis (%): C, 10.7; H, 2.88; N, 10.54; P, 2.98; Pt, 42.4

Theoretical value: C, 11.1; H, 2.79; N, 11.3; P, 3.57; Pt, 44.9

Proton nuclear magnetic resonance spectrum ($D_2O$, ppm): 2.7 (2H), 3.9 (1H)

Infrared spectrum (KBr cell, $cm^{-1}$): 534 (m), 808 (m), 982 (m), 1092 (m), 1140 (m), 1210 (m), 1314 (m), 1626 (s), 3128 (m), 3286 (s), 3363 (s)

EXAMPLE 6.

Synthesis of $[N_3P_3(L-Asp \cdot Pt(dach))_5(OCH_3)]$

After L-aspartic acid dimethyl ester(6.96 g, 43.2 mmol) was dissolved in 400 ml of anhydrous benzene and cooled to 0° C., 6.0 ml (43.2 mmol) of triethylamine was added to the solution, which was stirred for 30 minute. To this solution, 100 ml of anhydrous benzene solution containing 3.0 g(8.63 mmol) of hexachloro-cyclotriphosphazene was slowly added for 30 minutes and the reaction mixture was stirred for 20 hours at 70~80° C. After cooling the solution to room temperature, 0.53 ml (12.9 mmol) of methanol and 1.80 ml (12.9 mmol) of triethylamine were added and the solution mixture was stirred for 14 hours at 60~70° C. After filtering out the precipitate ($Et_3N \cdot HCl$), the solvent was evaporated at 40° C., and the product was eluted in dichloromethane through silica gel(mesh, 230~400) column to obtain purified viscous liquid product $[N_3P_3(L-Asp \cdot ME)_5 (OCH_3)]$. Yield:8.0 g (85%)

This intermediate cyclotriphosphazene derivative (3.0 g, 3.10 mmol) was suspended in 50 ml of aqueous solution containing 49.3 mmol of NaOH and stirred for 24 hours. The solution was filtered and the filtrate was freeze-dried. The solid product $[N_3P_3(L-Asp \cdot Na_2)_5(OCH_3)]$ was washed with sufficient amounts of methanol and ethylether and then dried(yield:90%).

The platinum intermediate $(dach)PtI_2$ (2.70 g, 4.80 mmol) and $AgNO_3$ (1.63 g, 9.60 mmol) were reacted in 30 ml of water for 10 hours and the resultant AgI was filtered off to obtain an aqueous solution of $(dach)Pt(NO_3)_2$. This solution was added dropwise to 30 ml of cold (0° C.) aqueous solution containing 1.0 g (0.96 mmol) of $[N_3P_3(L-Asp \cdot Na_2)_5(OCH_3)]$ and the reaction mixture was stirred in the dark for 20 minutes and for additional 20 minutes at 20° C. To remove the byproduct $NaNO_3$ in the reaction mixture, methanol was added and stirred for 30 minutes. After filtering out the precipitated $NaNO_3$, 500 ml of acetone was added to precipitate the final product. The precipitate was filtered, washed with acetone and ethylether and then dried under reduced pressure to obtain the final oligomeric platinum complex.

Molecular formula: $(C_{51}H_{93}N_{18}O_{21}P_3)Pt_5 \cdot 6(H_2O)$

Elemental analysis (%): C, 23.7; H, 5.10; N, 9.01; P, 2.98; Pt, 38.3

Theoretical value: C, 24.5; H. 4.28; N, 10.2; P, 3.76; Pt, 39.5

Proton nuclear magnetic resonance spectrum ($D_2O$, ppm): 1.1~1.3 (4H), 1.6 (2H), 2.2 (2H), 2.4~2.6 (4H), 3.4 (3H), 3.8 (1 H)

Infrared spectrum (KBr cell, $cm^{-1}$): 516 (m), 1032 (m), 1122 (m), 1173 (m), 1248 (m), 1302 (m), 1390 (s), 1585 (s), 2923 (m), 3212 (s), 3426 (s)

EXAMPLE 7.

Synthesis of [N3P3(L-Asp·Pt(dach))$_5$(NHCH$_3$)]

An oligomeric platinum complex was obtained by reacting 14 mmol of methylamine as a solubilizing agent, 2.70 g (4.80 mmol) of (dach)PtI$_2$, 1.63 g (9.60 mmol) of AgNO$_3$ and 1.0 g (0.96 mmol) of [NP(L-Asp·Na$_2$)$_5$(NHCH$_3$)] using the same procedure as described in Example 6.

Molecular formula: $(C_{51}H_{94}N_{19}O_{20}P_3)Pt_5 \cdot 6(H_2O)$

Elemental analysis (%): C, 24.8; H, 4.62; N, 9.8; P, 3.12; Pt, 39.8

Theoretical value: C, 24.8; H, 4.33; N, 10.8; P, 3.76; Pt, 39.5

Proton nuclear magnetic resonance spectrum ($D_2O$, ppm): 1.2~1.4 (4H), 1.6 (2H), 2.1 (2H), 2.4~2.6 (7H), 3.8 (1H)

Infrared spectrum (KBr cell, $cm^{-1}$): 518 (m), 904 (m), 1060 (m), 1114 (m), 1248 (m), 1307 (m), 1162 (m), 1387 (s), 1585 (s), 2923 (m), 3245 (s), 3385 (s)

EXAMPLE 8.

Synthesis of [NP(L-Glu·Pt(dach))$_2$]$_3$

An oligomeric platinum complex was obtained by reacting 3.0 g (8.63 mmol) of hexachlorocyclotriphosphazene, 13.6 g (77.7 mmol) of L-glutamic acid dimethyl ester, 10.8 ml (77.7 mmol) of triethylamine, 1.0 g (0.92 mmol) of [NP(L-Glu·Li$_2$)$_2$]$_3$, 3.12 g (5.54 mmol) of (dach)PtI$_2$ and 1.84 g (5.54 mmol) of Ag$_2$SO$_4$ using the same procedure as described in Example 1.

Molecular formula: $(C_{66}H_{120}N_{21}O_{24}P_3)Pt_6 \cdot 6(H_2O)$

Elemental analysis (%): C, 25.6; H. 4.21; N, 9.59; P, 2.68; Pt, 37.0

Theoretical value: C, 26.8; H. 4.49; N, 9.93; P, 3.14; Pt, 39.5

Proton nuclear magnetic resonance spectrum ($D_2O$, ppm): 1.1~1.3 (4H), 1.5 (2H), 2.0 (4H), 2.3 (4H), 3.7 (1H)

Infrared spectrum (KBr cell, $cm^{-1}$): 518 (m), 615 (m), 829 (m), 1033 (m), 1064 (m), 1170 (m), 1345 (m), 1400 (s), 1447 (m), 1578 (s), 2937 (m), 3234 (s), 3422 (s)

EXAMPLE 9.

Synthesis of [N$_3$P$_3$ (L-Glu·Pt(dach))$_5$(L-Glu·Li$_2$)]

An oligomeric platinum complex was obtained by reacting 2.59 g (4.60 mmol) of (dach)PtI$_2$, 1.53 g (4.60 mmol) of Ag$_2$SO$_4$ and 1.0 g (0.92 mmol) of [NP(L-Glu·Li$_2$)$_2$]$_3$ using the, Same procedure as described in Example 8.

Molecular formula: $(C_{60}H_{106}N_{19}O_{24}P_3)Li_2Pt_5 \cdot 6(H_2O)$

Elemental analysis (%): C, 26.6; H. 4.21; N, 9.59; P, 2.68; Pt, 37.0

Theoretical value: C, 27.0; H, 4.46; N, 9.98; P, 3.48; Pt, 36.6

Proton nuclear magnetic resonance spectrum ($D_2O$, ppm): 1.1~1.3 (4H), 1.5 (2H), 2.0 (4H), 2.3 (4H), 3.7 (1H)

Infrared spectrum (KBr cell, $cm^{-1}$): 518 (m), 615 (m), 829 (m), 1033 (m), 1064 (m), 1170 (m), 1345 (m), 1400 (s), 1447(m), 1575 (s), 2937(m), 3234 (s), 3422 (s)

EXAMPLE 10.

Synthesis of [N$_3$P$_3$(L-Glu·Pt(dach))$_3$(L-Glu·Li$_2$)$_3$]

An oligomeric platinum complex was obtained by reacting 1.55 g (2.76 mmol) of (dach)PtI$_2$, 0.91 g (2.76 mmol) of Ag$_2$SO$_4$ and 1.0 g (0.92 mmol) of [NP(L-Glu·Li$_2$)$_2$]$_3$ using the same procedure as described in Example 8.

Molecular formula: $(C_{48}H_{78}N_{15}O_{24}P_3)Li_6Pt_3 \cdot 6(H_2O)$

Elemental analysis (%): C, 26.6; H, 4.21; N, 9.59; P, 3.68; Pt, 27.5

Theoretical value: C, 27.8; H. 4.37; N, 10.1; P, 4.47; Pt, 28.2

Proton nuclear magnetic resonance spectrum ($D_2O$, ppm): 1.1~1.4 (4H), 1.6 (2H), 2.1 (4H), 2.5 (4H), 3.7 (1H)

Infrared spectrum (KBr cell, $cm^{-1}$): 530 (m), 620 (m), 829 (m), 1033 (m), 1064 (m), 1170 (m), 1345 (m), 1400 (s), 1447 (m), 1580 (s), 2937 (m), 3234 (s), 3422 (s)

EXAMPLE 11.

Synthesis of [NP(L-Glu·Pt(dmpda))$_2$]$_3$

An oligomeric platinum complex was obtained by reacting 3.05 g (5.54 mmol) of (dmpda)PtI$_2$, 1.84 g (5.54 mmol) of Ag$_2$SO$_4$ and 1.0 g (0.92 mmol) of [NP(L-Glu·Li$_2$)$_2$]$_{23}$ using the same procedure as described in Example 8.

Molecular formula: $(C_{60}H_{120}N_{21}O_{24}P_3)Pt_6 \cdot 6(H_2O)$

Elemental analysis (%): C, 23.8; H, 4.33; N, 10.7; P, 2.65; Pt, 39.5

Theoretical value: C, 24.9; H, 4.60; N, 10.2; P, 3.21; Pt, 40.5

Proton nuclear magnetic resonance spectrum ($D_2O$, ppm): 1.1 (6H), 2.2~2.6 (8H), 3.7 (1H)

Infrared spectrum (KBr cell, $cm^{-1}$): 530 (m), 826 (m), 1104 (m), 1116 (m), 1126 (m), 1384 (s), 1587 (s), 2960 (m), 3234 (s), 3385 (s)

EXAMPLE 12.

Synthesis of [NP(L-Glu·Pt(bampd))$_2$]$_3$

An oligomeric platinum complex was obtained by reacting 3.23 g (5.54 mmol) of (bampd)PtI$_2$, 1.84 g (5.54 mmol) of Ag$_2$SO$_4$ and 1.0 g (0.92 mmol) of [NP(L-Glu·Li$_2$)$_2$]$_3$ using the same procedure as described in Example 8.

Molecular formula: $(C_{60}H_{120}N_{21}O_{36}P_3)Pt_6 \cdot 6(H_2O)$

Elemental analysis (%): C, 22.8; H, 4.62; N, 10.1; P, 2.62; Pt, 36.2

Theoretical value: C, 23.4; H, 4.32; N, 9.56; P, 3.01; Pt, 37.9

Proton nuclear magnetic resonance spectrum ($D_2O$, ppm): 2.0~2.6 (8H), 3.3 (4H), 3.7 (1H)

Infrared spectrum (KBr cell, $cm^{-1}$): 532 (m), 834 (m), 1044 (m), 1228 (m), 1339 (m), 1400 (s), 1580 (s), 2925 (m), 3234 (s), 3404 (s)

EXAMPLE 13.

Synthesis of [NP(L-Glu·Pt(en))$_2$]$_3$

An oligomeric platinum complex was obtained by reacting 2.82 g (5.54 mmol) of (en)PtI$_2$, 1.84 g (5.54 mmol) of Ag$_2$SO$_4$ and 1.0 g (0.92 mmol) of [NP(L-Glu·Li$_2$)$_2$]$_3$ using the same procedure as described in Example 8.

Molecular formula: (C$_{42}$H$_{84}$N$_{21}$O$_{24}$P$_3$)Pt$_6$·6(H$_2$O)

Elemental analysis (%): C, 18.5; H, 4.01; N, 10.9; P, 2.95; Pt, 43.4

Theoretical value: C, 19.1; H, 3.67; N, 11.2; P, 3.52; Pt, 44.4

Proton nuclear magnetic resonance spectrum (D$_2$O, ppm): 2.1~2.6 (8H), 3.8 (1H)

Infrared spectrum (KBr cell, cm$^{-1}$): 570 (m), 768 (m), 1054 (m), 1189 (m), 1285 (m), 1400 (s), 1565 (s), 1638 (s), 3267 (m), 3450 (m)

EXAMPLE 14.

Synthesis of [NP(L-Glu·Pt(NH$_3$)$_2$)$_2$]$_3$

An oligomeric platinum complex was obtained by reacting 2.68 g (5.54 mmol) of (NH$_3$)$_2$PtI$_2$, 1.84 g (5.54 mmol) of Ag$_2$SO$_4$ and 1.0 g (0.92 mmol) of [NP(L-Glu·Li$_2$)$_2$]$_3$ using the same procedure as described in Example 8.

Molecular formula: (C$_{30}$H$_{72}$N$_{21}$O$_{24}$P$_3$)Pt$_6$·6(H$_2$O)

Elemental analysis (%): C, 12.7; H, 3.21; N, 10.1; P, 2.83; Pt, 41.9

Theoretical value: C, 13.4; H, 3.15; N. 10.9; P, 3.46; Pt, 43.6

Proton nuclear magnetic resonance spectrum (D$_2$O, ppm): 2.0 (2H), 2.4 (2H), 3.8 (1H)

Infrared spectrum (KBr cell, cm$^{-1}$): 540 (m), 836 (m), 1124 (m), 1178 (m), 1216 (m), 1350 (m), 1404 (s), 1578 (s), 2960 (m), 3266 (s)

EXAMPLE 15.

Synthesis of [N$_3$P$_3$(L-Glu·Pt(dach))$_5$(NHCH$_3$)]

An oligomeric platinum complex was obtained by reacting 14 mmol of methylamine as a solubilizing agent, 1.80 g (3.20 mmol) of (dach)PtI$_2$, 1.06 g (3.20 mmol) of Ag$_2$SO$_4$ and 1.0 g (0.64 mmol of [N$_3$P$_3$(L-Glu·Ba)$_5$(NHCH$_3$)] using the same procedure as described in Example 6.

Molecular formula: (C$_{56}$H$_{104}$N$_{19}$O$_{20}$P$_3$)Pt$_5$·6(H$_2$O)

Elemental analysis (%): C, 25.8; H, 5.23; N, 9.9; P, 2.96; Pt, 37.5

Theoretical value: C, 26.5; H, 4.60; N, 10.5; P, 3.66; Pt, 38.4

Proton nuclear magnetic resonance spectrum (D$_2$O, ppm): 1.1~1.3 (4H), 1.6 (2H), 2.0 (4H), 2.3~2.6 (7H), 3.8 (1H)

Infrared spectrum (KBr cell, cm$^{-1}$): 518 (m), 614 (m), 904 (m), 1060 (m), 1082 (m), 1201 (m), 1248 (m), 1307 (m), 1403 (s), 1580 (s), 2938 (m), 3194 (s) 3418 (s)

EXAMPLE 16.

Synthesis of [NP(Am·Pt(dach)$_2$]$_3$

An oligomeric platinum complex was obtained by reacting 3.0 g (8.63 mmol) of hexachlorocyclotriphosphazene, 13.6 g (77.7 mmol) of amino malonic acid dimethyl ester, 3.65 g (6.48 mmol) of (dach)PtI$_2$, 2.15 g (6.48 mmol) of Ag$_2$SO$_4$ and 1.0 g (1.08 mmol) of [NP(Am·Li$_2$)$_2$]$_3$ using the same procedure as described in Example 1.

Molecular formula: (C$_{54}$H$_{72}$N$_{21}$O$_{24}$P$_3$)Pt$_6$·6(H$_2$O)

Elemental analysis (%): C, 22.7; H, 3.01; N, 9.82; P, 2.88; Pt, 40.5

Theoretical value: C, 23.2; H, 3.03; N, 10.5; P, 3.32; Pt, 41.9

Proton nuclear magnetic resonance spectrum (D$_2$O, ppm): 1.1~1.3 (4H), 1.5 (2H), 2.0 (2H), 2.3 (2H), 3.9 (1H)

Infrared spectrum (KBr cell, cm$^{-1}$): 503 (m), 775 (m), 931 (m), 1034 (m), 1108 (m), 1173 (m), 1243 (m), 1342 (s), 1453 (m), 1641 (s), 2923 (m), 3208 (s), 3414 (s)

EXAMPLE 17.

Synthesis of [NP(Am·Pt(dmpda))$_2$]$_3$

An oligomeric platinum complex was obtained by reacting 3.57 g (6.48 mmol) of (dmpda)PtI$_2$, 2.15 g (6.48 mmol) of Ag$_2$SO$_4$ and 1.0 g (1.08 mmol) of [NP(Am·Li$_2$)$_2$]$_3$ using the same procedure as described in Example 16.

Molecular formula: (C$_{48}$H$_{96}$N$_{21}$O$_{24}$P$_3$)Pt$_6$·6(H$_2$O)

Elemental analysis (%): C, 21.8; H, 4.33; N, 10.7; P, 2.65; Pt, 41.5

Theoretical value: C, 21.2; H, 4.0; N, 10.8; P, 3.41; Pt, 43.0

Proton nuclear magnetic resonance spectrum (H$_2$O, ppm): 1.1 (6H), 2.3~2.5 (4H), 3.7 (1H)

Infrared spectrum (KBr cell, cm$^{-1}$): 518 (m), 620 (m), 1116 (m), 1167 (m), 1384 (s), 1638 (s), 2945 (m), 3234 (s), 3446 (s)

EXAMPLE 18.

Synthesis of [NP(Am·Pt(en))$_2$]$_3$

An oligomeric platinum complex was obtained by reacting 3.30 g (6.48 mmol) of (en)PtI$_2$, 2.15 g (6.48 mmol) of Ag$_2$SO$_4$ and 1.0 9 (1.08 mmol) of [NP(Am·Li$_2$)$_2$]$_3$ using the same procedure as described in Example 16.

Molecular formula: (C$_{30}$H$_{60}$N$_{21}$O$_{24}$P$_3$)Pt$_6$·6(H$_2$O)

Elemental analysis (%): C, 14.1; H, 3.01; N, 11.2; P, 2.95; Pt, 46.4

Theoretical value: C, 14.6; H, 2.94; N, 11.9; P, 3.76; Pt, 47.4

Proton nuclear magnetic resonance spectrum (D$_2$O, ppm): 2.3 (4H), 3.8 (1H)

Infrared spectrum (KBr cell, cm$^{-1}$): 570 (m), 765 (m), 1049 (m), 1128 (m), 1291 (m), 1400 (s), 1638 (s), 3267 (m), 3450 (m)

Toxicity test

A pilot acute toxicity test was performed for the compound (KI-60606) described in Example 8 of the present invention by intravenous injection.

1. Test material
   (1) compound: KI-60606
   (2) carrier: physiological saline for injection
2. Test animal
   (1) animal model: ICR mouse
   (2) age of the animal: 4 weeks old when delivered, 5 weeks old when the drug was administered
   (3) sex and number of animals: 12 males and 12 females
   (4) breeding condition: temperature: 23 3C. relative humidity: 50 10% light intensity: 150–300 Lux
3. Number and method of administration: single tail vein injection
4. Amount of administration: 62.5, 125, 250, 500, 1000, 2000 mg/kg for each male or female
5. Observation categories: general symptoms, symptoms of dead animals, body weight up to seventh day after administration, autopsy finding.
6. Results
   (1) Results of death rate test are summarized in Table 1.

TABLE 1

| Sex | Dose (mg/kg) | Number of animals | \multicolumn{8}{c}{Day after administration} | Death rate (%) | Estimated LD$_{50}$ value (mg/Kg) |
|---|---|---|---|---|---|---|---|---|---|---|---|---|
| | | | 0 | 1 | 2 | 3 | 4 | 5 | 6 | 7 | | |
| Male | 62.5 | 2 | | | | | | | | | 0 | 125 |
| | 125 | 2 | | 1 | | | | | | | 50 | |
| | 250 | 2 | | 2 | | | | | | | 100 | |
| | 500 | 2 | | 2 | | | | | | | 100 | |
| | 1000 | 2 | | 2 | | | | | | | 100 | |
| | 2000 | 2 | | 2 | | | | | | | 100 | |
| Female | 62.5 | 2 | | | | | | | | | 0 | 125~250 |
| | 125 | 2 | | | | | | | | | 0 | |
| | 250 | 2 | | 2 | | | | | | | 100 | |
| | 500 | 2 | | 2 | | | | | | | 100 | |
| | 1000 | 2 | | 2 | | | | | | | 100 | |
| | 2000 | 2 | | 2 | | | | | | | 100 | |

(2) General Symptoms

The group of male or female mice administered with 500 mg/kg or more died 10–20 seconds after injection. These mice had symptoms including prone positioning, gait disturbance and dyspnea. The dead mice after administration of 125 or 250 mg/kg of drug had symptoms including prone positioning and drooling. The live animals did not have any particular symptoms one day after injection.

(3) Body weight

Decrease in the body weight was observed in 2 female mice that had 125 mg/kg dose and in 1 male mouse that had 62.5 mg/kg dose.

(4) autopsy finding

No particular autopsy finding was observed for the mice that died immediately after administration or for the mice that survived for the whole test period.

7. Summary

To obtain information on acute toxicity of KI-60606, the drug at the doses of 62.5, 125, 250, 500, 1000, 2000 mg/kg each was administered via single intravenous injection to ICR mice. The LD$_{50}$ was estimated to be 125 mg/kg for male and 125–250 mg/kg for female. Main symptoms include prone positioning, gait disturbance, dyspnea and decrease in body weight.

Example of anticancer activity test

To groups of 8 BDF1 mice (6 to 8 week-old), 1×106 leukemia L1210 cells were implanted per mouse. After dissolving appropriate amounts of the platinum complex in 0.9% physiological saline, 1–20 mg/kg was administered via intra-peritoneal injection at days 1, 5 and 9 to observe the increased life span (ILS, %) and number of survival. The results are summarized in Table 2.

TABLE 2

Test results for the anticancer activity against mouse leukemia L1210 cells

| Compounds | Dose (mg/kg) | Increased life span (ILS, %) | Number of survival after 60 days |
|---|---|---|---|
| Example 1 | 60 | >448.8 | 4/8 |
| | 40 | >243.8 | 1/8 |
| Example 2 | 60 | 147.9 | |
| | 30 | 165.0 | |
| Example 4 | 60 | Toxic | |
| | 30 | 250.9 | |
| Example 8 | 80 | >402.8 | 3/8 |
| | 60 | >400 | 3/8 |

TABLE 2-continued

Test results for the anticancer activity against mouse leukemia L1210 cells

| Compounds | Dose (mg/kg) | Increased life span (ILS, %) | Number of survival after 60 days |
|---|---|---|---|
| Example 13 | 60 | Toxic | |
| | 30 | 277 | |
| Example 16 | 60 | Toxic | |
| | 30 | 222.1 | |
| Example 18 | 60 | Toxic | |
| | 30 | >400 | 3/8 |
| Cisplatin | 4 | 60 | |
| Carboplatin | 40 | 80 | |

Example of anaphylaxis test

To observe anaphylactic reaction of the drug, induced antigens were injected at day 14 of the final drug administration to the rear foot of the groups of 5 Hartley guinea pigs. The systemic symptoms were observed 30 minutes after the injection. As shown in Table 3, all of the animals administered with polymeric platinum complex (KI-30606) died due to anaphylaxis. However, only 2 animals administered with oligomeric platinum complex of the present invention (KI 60606: The compound in Example 8 of the present invention) had severe symptoms but none died. Moreover, the antigenicity was even less for these groups than for those administered with physiological saline solution showing that the anaphylactic reaction is not present for the oligomeric platinum complex.

TABLE 3

Results of guinea pig anaphylaxis test

| Antigen* | Induced antigen* | Number of animals | \multicolumn{5}{c}{Symptom} |
|---|---|---|---|---|---|---|---|
| | | | [−] | [] | [+] | [++] | [+++] |
| KI-30606 (1 mg/kg) | KI-30606 (5 mg/kg) | 5 | | | | | 5 |
| KI-30606 (5 mg/kg) | KI-30606 (5 mg/kg) | 4 | | | | | 4 |
| KI-60606 (1 mg/kg) | KI-60606 (5 mg/kg) | 4 | | 1 | 1 | 2 | |

TABLE 3-continued

Results of guinea pig anaphylaxis test

| Antigen* | Induced antigen* | Number of animals | Symptom | | | | |
|---|---|---|---|---|---|---|---|
| | | | [−] | [] | [+] | [++] | [+++] |
| KI-60606 (5 mg/kg) | KI-60606 (5 mg/kg) | 4 | 3 | | 1 | | |
| Saline (1 mg/kg) | saline (1 mg/kg) | 5 | 1 | | 4 | | |

[−]: asymptomatic
[±]: mild
[+]: moderate
[++]: severe
[+++]: death
*KI-30606: [NP(OH)(Glu.Pt(dach)]n
*KI-60606: [NP(Glu.Pt(dach))2]3

Conclusion: Oligomeric platinum complex of the present invention has no anaphylactic reaction and a lower toxicity than conventional platinum anticancer drugs. Moreover, oligomeric platinum complex of the present invention is expected to be a promising anticancer drug due to its superior anticancer activity.

What is claimed is:

1. A platinum complex conjugated to cyclotriphosphazene represented by Formula 1:

Formula 1

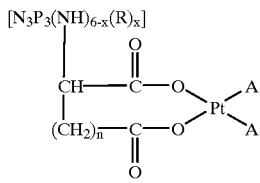

(wherein $N_3P_3$ is a cyclotriphosphazene backbone

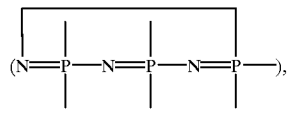

R is a solubilizing agent selected from the group consisting of methylamine, methoxy and amino acid;

A is a monodentate neutral ligand ammonia ($NH_3$) or as

represents a bidentate chelating diamine selected from the group consisting of ethylenediamine ($NH_2CH_2CH_2NH_2$) (en), 2,2-dimethyl-1,3-propanediamine ($NH_2CH_2CH(CH_3)_2CH_2NH_2$)(dmpda), 2,2-bisaminomethylpropanediol ($NH_2CH_2C(CH_2OH)_2CH_2NH_2$)(bampd), and trans-(±)-1,2-diaminocyclohexane

n is the number defining the kind of anionic amino carboxylic acids and is an integer from 0 to 2; wherein 0 for amino malonic acid derivatives, 1 for aspartic acid derivatives and 2 for glutamic acid derivatives; and x is a value between 0 and 3).

2. A platinum complex conjugated to cyclotriphosphazene according to the claim 1 wherein x is 0 or 3.

3. A method for preparing an oligomeric platinum complex of formula 1

Formula 1

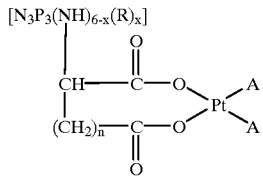

wherein $N_3P_3$ is a cyclotriphosphazene backbone

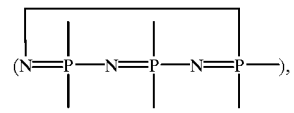

R is a solubilizing agent selected from the group consisting of methylamine, methoxy and amino acid;

A is a monodentate neutral ligand ammonia ($NH_3$) or as

represents a bidentate chelating diamine selected from the group consisting of ethylenediamine ($NH_2CH_2CH_2NH_2$) (en), 2,2dimethyl-1,3-propanediamine ($NH_2CH_2CH(CH_3)_2CH_2NH_2$(dmpda), 2,2-bisaminomethylpropanediol ($NH_2CH_2C(CH_2OH)_2CH_2NH_2$)(bampd), and trans-(±)-1,2-diaminocyclohexane

n is the number defining the kind of anionic amino carboxylic acids and is an integer from 0 to 2; wherein 0 for amino malonic acid derivatives, 1 for aspartic acid derivatives and 2 for glutamic acid derivatives; and x is a value between 0 and 3, comprising following steps; (1) substitution of hexachlorocyclotriphosphazene with a dicarboxylic amino acid and a solubilizing agent, followed by hydrolysis to obtain an alkali metal salt of Formula 3 or alkaline earth metal salt of Formula 4; (2) reacting the salt of Formulas 3 or 4 with (diamine)platinum salt of Formula 5 in a mole ratio of 1:3~6 in aqueous solution at room temperature to obtain the oligomeric platinum complex of Formula 1

Formula 3

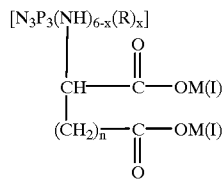

Formula 4

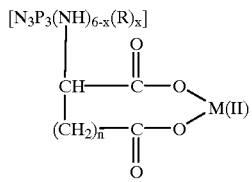

Formula 5

wherein R, A, x and n are identical to those defined as in Formula 1;

M(I) is an alkali metal ion;

M(II) is an alkaline earth metal ion;

$L_2$ is an anion selected from two $NO_3^-$ ions or a single $SO_4^{2-}$ ion.

4. The method according to claim 3 wherein the dicarboxylic amino acid derivative is selected from the group consisting of methyl esters or ethylesters of amino malonic acid, aspartic acid and glutamic acid; and the solubilizing agent is selected from the group consisting of methoxy group, methylamine and alkali metal or alkali earth metal salts of amino carboxylic acids.

5. The method according to claim 3 wherein the alkali metal of the Formula 3 is lithium or sodium, the alkaline earth metal of the Formula 4 is barium or calcium; and the platinum salt of Formula 5 is (diamine)platinum sulfate or (diamine)platinum nitrate.

6. The method according to claim 5 which comprises reacting alkali metal salt of Formula 3 and (diamine)platinum (II) sulfate of Formula 5 in a mole ratio of 1:3~6 in aqueous solution, adding barium chloride equimolar to (diamine)platinum(II) resultind in precipitation of barium sulfate which is filtered out and then adding organic solvent.

7. The method according to claim 6 wherein the organic solvent is selected from the group consisting of acetone, ethanol, methanol and their mixture.

8. An anticancer agent comprising the platinum complex of formula 1 as an active ingredient:

Formula 1

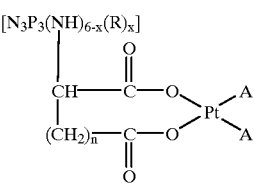

(wherein $N_3P_3$ is a cyclotriphosphazene backbone

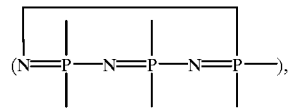

R is a solubilizing agent selected from the group consisting of methylamine, methoxy and amino acid;

A is a monodentate neutral ligand ammonia (NH3) or as

represents a bidentate chelating diamine selected from the group consisting of ethylenediamine ($NH_2CH_2CH_2NH_2$) (en), 2,2-dimethyl-1,3-propanediamine ($NH_2CH_2CH(CH_3)_2CH_2NH_2$)(dmpda), 2,2-bisaminomethylpropanediol ($NH_2CH_2C(CH_2OH)_2CH_2NH_2$)(bampd), and trans-(±)-1,2-diaminocyclohexane

n is the number defining the kind of anionic amino carboxylic acids and is an integer from 0 to 2; wherein 0 for amino malonic acid derivatives, 1 for aspartic acid derivatives and 2 for glutamic acid derivatives; and x is a value between 0 and 3).

* * * * *

UNITED STATES PATENT AND TRADEMARK OFFICE
CERTIFICATE OF CORRECTION

PATENT NO. : 6,221,906 B1
DATED : April 24, 2001
INVENTOR(S) : Youn Soo Sohn *et al.*

It is certified that error appears in the above-identified patent and that said Letters Patent is hereby corrected as shown below:

Title page,
In [73] Assignee:
      Add -- and Il-Yang Pharm. Co., Ltd., Kyunggi-do (KR) --

Signed and Sealed this

Twenty-third Day of October, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 6,221,906 B1
DATED         : April 24, 2001
INVENTOR(S)   : Youn Soo Sohn et al.

It is certified that error appears in the above-identified patent and that said Letters Patent is hereby corrected as shown below:

<u>Title page,</u>
Item [75], Inventors, change the city of inventor Chong Ock Lee from "Seoul" to
-- Daejon --.

Signed and Sealed this

Tenth Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,221,906 B1
DATED         : April 24, 2001
INVENTOR(S)   : Youn Soo Sohn et al.

It is certified that error appears in the above-identified patent and that said Letters Patent is hereby corrected as shown below:

<u>Title page,</u>
Item [75], Inventors, change the city of inventor Chong Ock Lee from "Seoul" to -- Daejon --.

Signed and Sealed this

Eighth Day of October, 2002

Attest:

JAMES E. ROGAN
Attesting Officer    Director of the United States Patent and Trademark Office